United States Patent
Haar et al.

(10) Patent No.: US 7,276,027 B2
(45) Date of Patent: Oct. 2, 2007

(54) SYSTEM, FOR MONITORING THE CONCENTRATION OF ANALYTES IN BODY FLUIDS

(75) Inventors: Hans-Peter Haar, Wiesloch (DE); Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 241 days.

(21) Appl. No.: 10/467,592

(22) PCT Filed: Feb. 2, 2002

(86) PCT No.: PCT/EP02/01091

§ 371 (c)(1),
(2), (4) Date: Jul. 14, 2004

(87) PCT Pub. No.: WO02/062210

PCT Pub. Date: Aug. 15, 2002

(65) Prior Publication Data

US 2004/0249311 A1  Dec. 9, 2004

(30) Foreign Application Priority Data

Feb. 6, 2001 (DE) ............................. 101 05 549

(51) Int. Cl.
*A61B 5/00* (2006.01)
(52) U.S. Cl. ........................... 600/309; 600/584
(58) Field of Classification Search ........... 600/309, 600/322, 341, 362, 365, 367
See application file for complete search history.

(56) References Cited

U.S. PATENT DOCUMENTS

| 1,458,958 | A | | 6/1923 | Schneider |
| 3,651,807 | A | | 3/1972 | Huggins |
| 4,199,261 | A | | 4/1980 | Tidd et al. ............. 356/448 |
| 4,218,421 | A | | 8/1980 | Mack, Jr. et al. ......... 422/66 |
| 4,265,249 | A | | 5/1981 | Schindler et al. |
| 4,336,544 | A | | 6/1982 | Donald et al. ........... 346/1.1 |
| 4,777,953 | A | | 10/1988 | Ash et al. |
| 4,832,034 | A | | 5/1989 | Pizziconi et al. |
| 4,852,025 | A | | 7/1989 | Herpichbohm |
| 4,871,351 | A | | 10/1989 | Feingold ................. 604/66 |
| 4,989,606 | A | * | 2/1991 | Gehrich et al. .......... 600/312 |

(Continued)

FOREIGN PATENT DOCUMENTS

DE  2131334  6/1971

(Continued)

*Primary Examiner*—Eric F Winakur
(74) *Attorney, Agent, or Firm*—Barnes & Thornburg LLP

(57) ABSTRACT

The invention concerns a system for monitoring the concentration of analytes in body fluids, in particular in interstitial fluid and comprises a catheter having an implantable region and an outlet opening for withdrawing fluid in particular body fluid. A first and a second analytical zone are contacted sequentially with fluid from the catheter and undergo a detectable change when an analyte is present. The analytical zones can be contacted manually with fluid and also preferably in an automated fashion by means of a device. A system according to the invention additionally has an analytical device for analysing the analytical zones in order to determine the concentration of the analyte on the basis of changes caused by the analyte. A further subject matter of the present invention are catheters for use in systems according to the invention as well as magazines containing test zones.

17 Claims, 6 Drawing Sheets

U.S. PATENT DOCUMENTS

| | | | |
|---|---|---|---|
| 5,035,704 A * | 7/1991 | Lambert et al. | 606/182 |
| 5,114,350 A | 5/1992 | Hewett | 435/288 |
| 5,174,291 A | 12/1992 | Schoonen et al. | |
| 5,288,636 A | 2/1994 | Pollmann et al. | 435/288 |
| 5,335,658 A | 8/1994 | Bedingham | |
| 5,368,029 A | 11/1994 | Holcombe et al. | |
| 5,496,300 A | 3/1996 | Hirsch et al. | 604/327 |
| 5,582,184 A | 12/1996 | Erickson et al. | |
| 5,679,311 A * | 10/1997 | Harttig et al. | 422/102 |
| 5,682,233 A * | 10/1997 | Brinda | 356/246 |
| 5,746,217 A | 5/1998 | Erickson et al. | |
| 5,820,570 A | 10/1998 | Erickson et al. | 600/573 |
| 5,823,973 A | 10/1998 | Racchini et al. | 600/573 |
| 5,902,253 A | 5/1999 | Pfeiffer et al. | |
| 5,947,911 A * | 9/1999 | Wong et al. | 600/573 |
| 6,029,919 A | 2/2000 | Rousseau | 241/101.2 |
| 6,036,919 A | 3/2000 | Thym et al. | 422/58 |
| 6,045,541 A | 4/2000 | Matsumoto et al. | |
| 6,988,996 B2 * | 1/2006 | Roe et al. | 600/584 |

FOREIGN PATENT DOCUMENTS

| | | |
|---|---|---|
| DE | 3112762 A1 | 1/1983 |
| DE | 3908123 A1 | 9/1990 |
| DE | 19819407 A1 | 11/1999 |
| EP | 0256806 | 2/1988 |
| EP | 0366336 | 5/1990 |
| EP | 0373413 | 6/1990 |
| EP | 0401179 | 12/1990 |
| EP | 0926484 A2 | 6/1999 |
| EP | 0992287 A2 | 4/2000 |
| JP | 9-504726 | 5/1997 |
| JP | 10-62434 | 3/1998 |
| WO | WO 83/00931 | 3/1983 |
| WO | WO 91/16416 | 10/1991 |
| WO | WO 95/20991 | 8/1995 |
| WO | WO 96/05875 | 2/1996 |
| WO | WO 97/14468 | 4/1997 |
| WO | WO 00/13580 | 3/2000 |
| WO | WO 00/22977 A1 | 4/2000 |

* cited by examiner

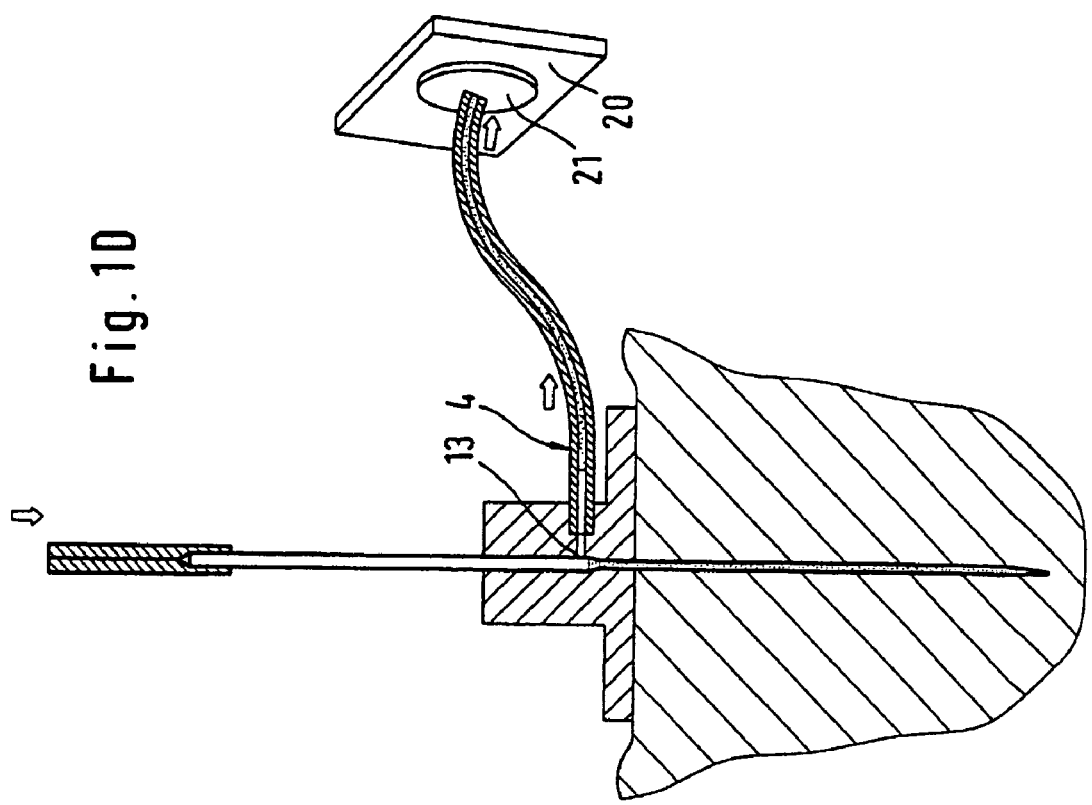
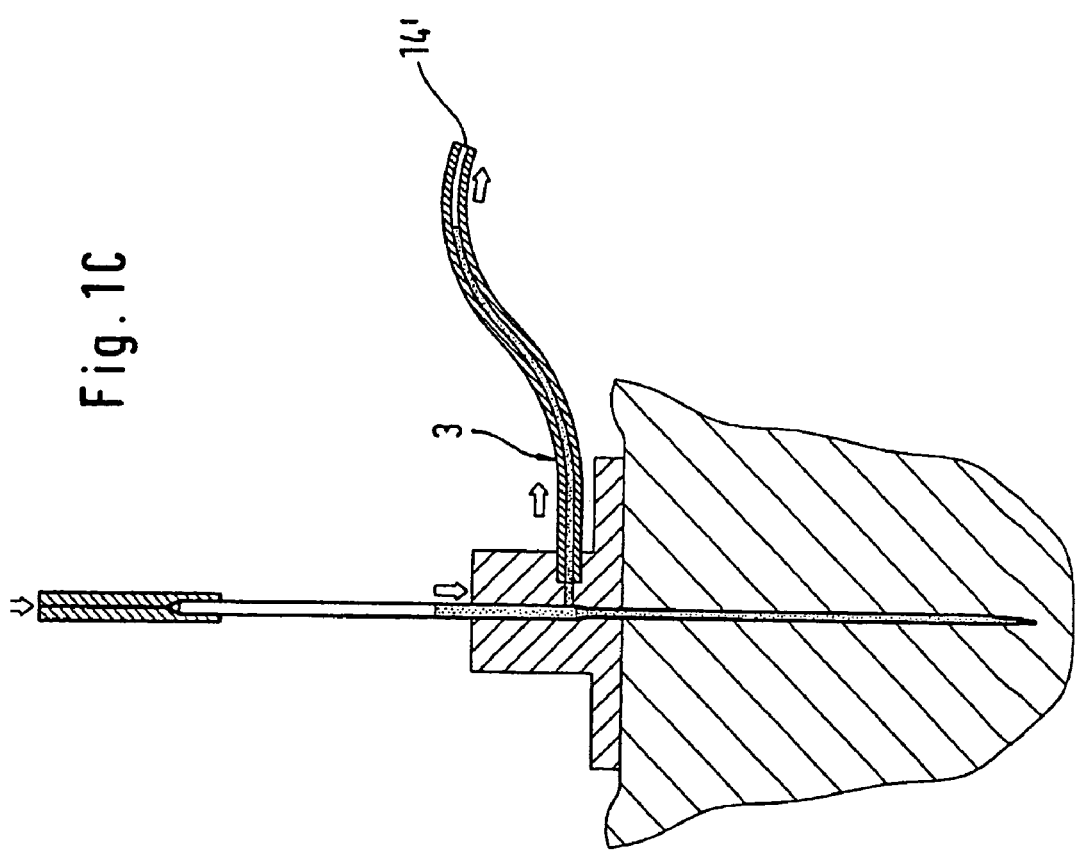

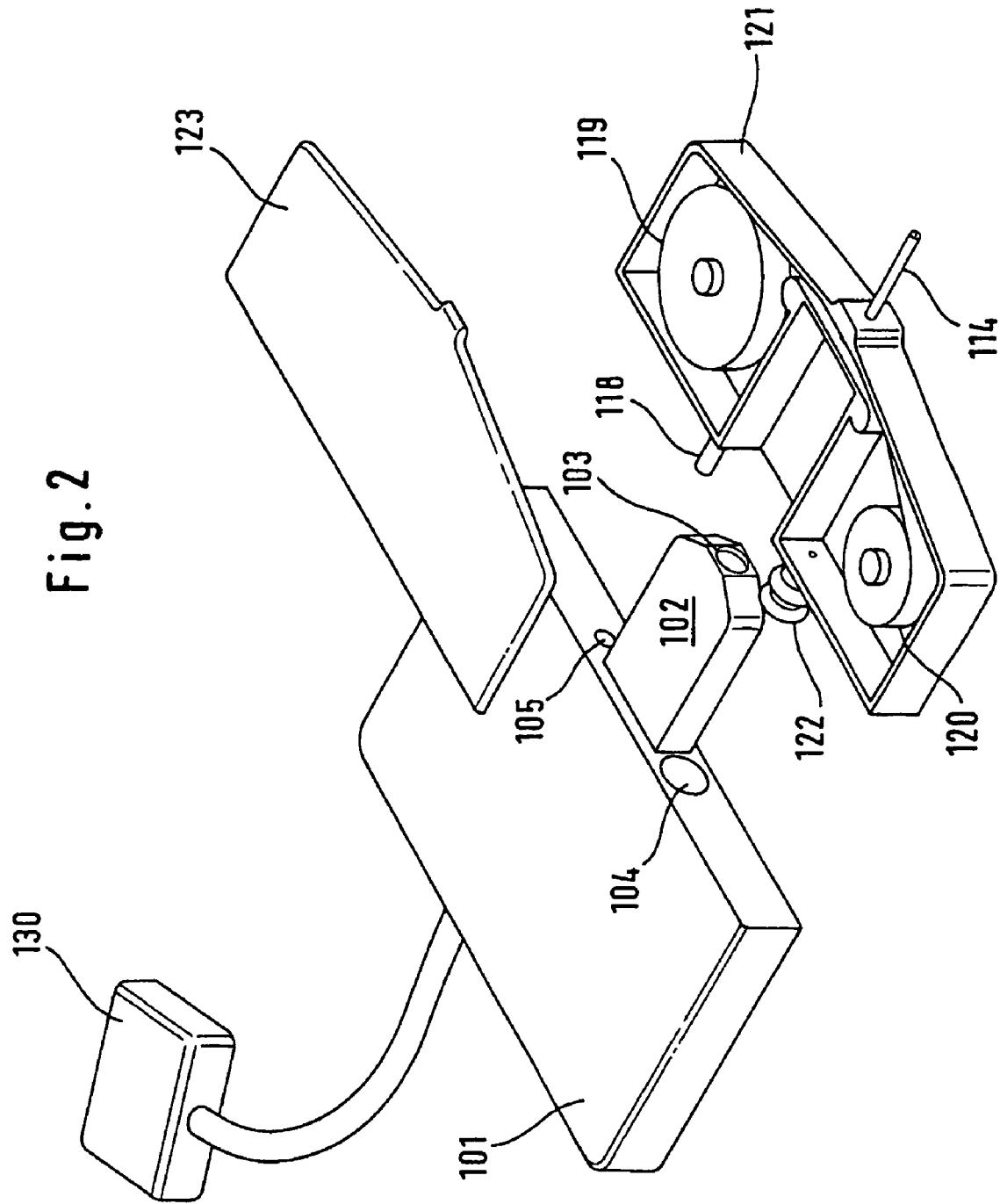

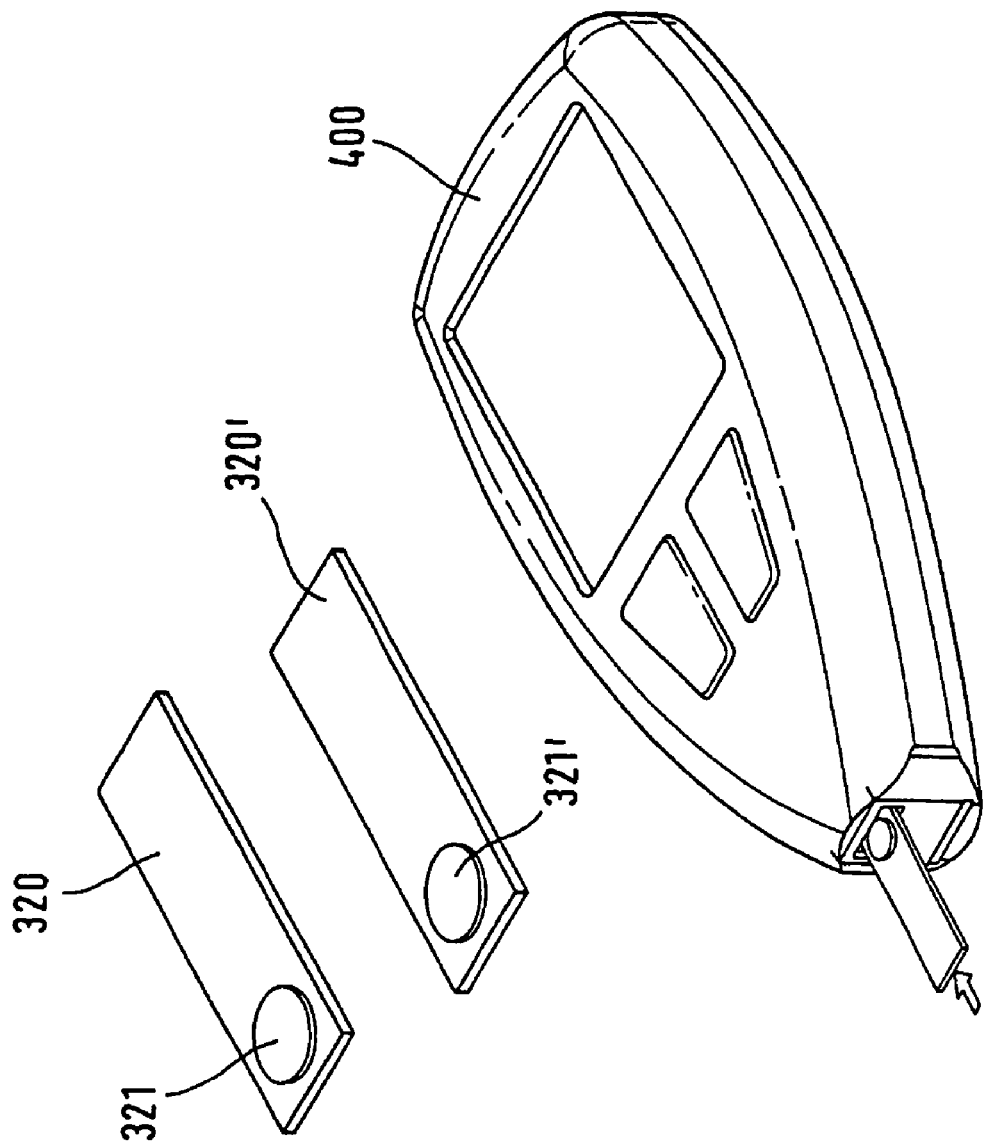
Fig. 5
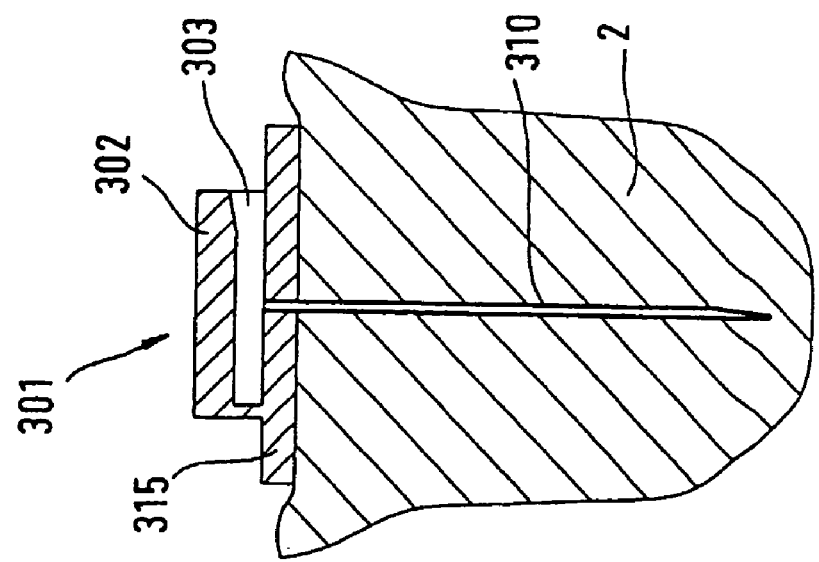

SYSTEM, FOR MONITORING THE CONCENTRATION OF ANALYTES IN BODY FLUIDS

TECHNICAL FIELD

The present invention is in the field of diagnosis in which body fluids are withdrawn and analysed for the presence or concentration of analytes.

BACKGROUND

Numerous methods are known in the prior art for monitoring analyte concentrations in body fluids. On the one hand there are systems in which blood is withdrawn by a catheter and conveyed to a measuring cell. The document WO 91/16416 which describes an instrument that can be carried on the arm that withdraws blood samples by means of a catheter implanted in a blood vessel is mentioned as a representative of such procedures. The sample liquid is conveyed through an essentially closed channel system to an enzyme electrode which is designed to carry out a multitude of measurements. The system described in this document and other systems based on electrochemical sensors that measure continuously, have the disadvantage that the sensors have a pronounced signal drift. This becomes particularly obvious from the document WO 91/16416 when the laborious calibration is taken into consideration. Another disadvantage of such sensor-based systems is that relatively large amounts of fluids are required. In the prior art sensors are known as systems that only require small amounts of liquid and thus this statement is initially surprising. However, when emphasising the positive features of sensor systems, one often does not take into account that fluid channels are necessary and a sensor surface of sufficient size has to be wetted.

Ultrafiltration devices are also known in the prior art of which the documents U.S. Pat. No. 4,832,034 and U.S. Pat. No. 4,777,953 are mentioned as examples. These systems also use electro-chemical sensors and thus also have the above-mentioned disadvantages. In addition there are disadvantages which are caused by the ultrafiltration membrane. It is critical to select a suitable membrane material which has the combined properties of an adequately high filtration effect and permeability and does not already become blocked after a short period.

Another procedure for monitoring analyte concentrations is known under the name microdialysis. Representative documents from this field are: U.S. Pat. No. 5,174,291, EP 0 401 179 and U.S. Pat. No. 4,265,249. Flow measuring cells with electrochemical sensors are used in the arrangements described in these documents. Although the ultrafiltration problems caused by membranes are less with microdialysis, microdialysis systems have the disadvantage that a perfusion liquid has to be pumped through a hollow catheter. The provision of solutions, the pumping process and the construction of the catheter are technical' complications which increase the complexity.

The methods described above for monitoring analyte concentrations in body fluids are based on the premise that the monitoring requires a continuous or at least a more or less continuous measurement at relatively short time intervals. This explains the exclusive use of sensors that operate continuously in flow measuring cells.

Discontinuous concepts are also known in the field of analyte concentration monitoring. For example diabetics carry out several discrete measurements during a day in order to monitor their blood glucose level. For this purpose is it customary to firstly make an incision with a lancet and to apply the emerging blood to a disposable test element. This is analysed with a suitable device in order to determine the blood glucose concentration. Optical systems as well as systems that use electrochemical test elements are known in the prior art. Devices have also been known for some time in which the incision, sample collection and sample application can be carried out with a single disposable test element. Such systems for determining blood glucose in interstitial fluid are described for example in the documents U.S. Pat. No. 5,746,217, U.S. Pat. No. 5,823,973 and U.S. Pat. No. 5,820,570. The aforementioned devices have a thin cannula which is inserted into the dermis and collects interstitial fluid at this site. The cannula conveys the liquid onto a test element. A disadvantage of this system is that a cannula has to be inserted again for each individual measurement. In addition to the discomfort caused by the repeated piercing, the user has to carry out a number of operating steps such as inserting a disposable element into an apparatus, starting the lancing process, waiting until the result of the analysis is displayed and replacing the test element. Moreover the said devices have to be carried around by the user and he has to find a discreet place to carry out the measurement if he does not want to publicly exhibit his disease.

A system which also has the aforementioned disadvantages, but which uses a system comprising a catheter and an initially separate test element is described in U.S. Pat. No. 5,368,029. According to this document a catheter is firstly introduced into a blood vessel and one waits until a transparent chamber is filled with blood (flushing). Then a disposable test element is inserted into the chamber through a valve slit in order to bring the test element into contact with the blood. It is hardly conceivable that such a system could be used routinely by a diabetic since it is necessary to introduce a catheter into a blood vessel with a considerable risk of infection and injury. In addition a relatively large amount of sample is required. The description in the document shows that the system is designed to be used in emergency medicine. Another essential disadvantage of the concept is that the system does not enable monitoring of an analyte concentration but only allows a single measurement which reflects the momentary concentration level. The document contains no information or suggestions whatsoever on how to carry out repeated measurements by coupling new test elements. This is logical since the blood collected in the chamber is not exchanged and thus subsequent measurements with additional test elements would only yield the same measured value and not a measured value that would lead to a later concentration value.

SUMMARY

The present invention is based on systems with sensors that operate continuously as well as on systems with separate lancing processes. The invention concerns a system for monitoring the concentration of analytes in body fluids, in particular in interstitial fluid and comprises a catheter with an implantable region and an outlet aperture for withdrawing fluid, in particular body fluid. A first and a second analytical zone are contacted successively with fluid from the catheter and undergo a detectable change when an analyte is present. The contacting of the analytical zones with fluid can be achieved manually and also preferably automatically by means of a device. A system according to the invention additionally has an analytical device to analyse the analytical zones in order to determine the concentration of the analyte on the basis of the changes caused by the analyte. The present invention additionally concerns catheters for use in systems according to the invention and magazines with test zones.

The present invention combines the advantages of continuously operating systems with those of individual measurements using disposable test elements. The invention utilizes a catheter which remains implanted between the (at least two) measurements and hence it is not necessary to make repeated incisions as is the case with previous systems with disposable test elements. Problems of previous continuously operating systems which are mainly coupled to the use of continuously operating sensors are avoided by using separate test elements. However, this combination of known elements has neither been previously described in the prior art nor made obvious to a person skilled in the art. Previously experts have assumed that measurements have to be carried out at short time intervals for a continuous monitoring of the analyte concentration which necessitates the use of flow measuring cells containing continuously operating sensor systems. Initially the provision of such a large number of analyses at short time intervals appears to be incompatible with disposable test elements. The concept according to the invention revolutionizes the monitoring of analyte concentrations because the monitoring can be carried out with a relatively simple system which is in particular free from the drift of electrochemical sensors. Dry chemistry test elements can be used for the test elements or test zones which have already proven in practice to be particularly suitable with regard to accuracy and precision and are advantageous to manufacture.

The system and method according to the invention are used to monitor analyte concentrations in body fluids. Analytes that can be monitored using the present invention are for example glucose, lactate, electrolytes, pharmaceutically active substances and such like. Body fluids in the sense of the invention are in particular interstitial fluid and blood. If interstitial fluid is used, fluid is preferred which has been obtained from a depth of >1 mm under the skin surface since at this position there is a good and sufficiently fast exchange with the blood transport system.

A catheter with an implantable region is used to withdrawn fluid. Catheters within the sense of this invention are tubes into which the body fluid enters and can be removed from an outlet opening and also devices with a semipermeable membrane and hence the fluid entering the catheter is not a body fluid in a strict sense but a fluid that has already been pretreated (ultrafiltrate). In principle it is also possible to use a microdialysis catheter as a catheter which operates with perfusion fluid and takes up analyte from the interior of the body by diffusion and yields dialysate. Catheters with a semipermeable membrane or a microporous wall have the advantage that cells and even larger molecules interfering with detection may be excluded. It is therefore preferred to employ membranes or microporous walls with a pore size below 500 nm.

However, a problem with a microdialysis catheter circulating dialysis fluid is that fluid emerging from the catheter may under certain circumstances not reflect the true analyte concentration inside the body but rather only a fraction thereof when the residence times are short. Consequently catheters are preferred for the invention which are designed such that body fluid flows directly out of them (as e.g. in case of ultrafiltration) which may also be freed from cells.

The term catheter is used in the scope of this invention not only for the part that is implanted in the body but rather the term catheter should also encompass the fluid connections and other connected parts that belong to such a part. In the simplest case the catheter can be composed of a thin hollow needle or a tubing one end of which is inserted into the body and from the other end of which, the outlet opening, a body fluid flows out. Tubing or such like can be coupled to such a catheter so that as a result the outlet opening is shifted to the corresponding end of the tubing. The structure and function of suitable or preferred catheters is described in more detail in conjunction with the figures. It may be advantageous to use a so-called applicator device to insert the implantable region of the catheter into the body. In this manner it is also possible to construct the implantable region with a very small diameter down to e.g. 100 µm. Even materials like steel are flexible in this thickness range. If an applicator device were not used, flexible constructions would have been eliminated for practical reasons due to the impossibility of introducing them into the body. Suitable applicator devices for flexible and also for rigid arrangements are known in the prior art. U.S. Pat. No. 3,651,807; EP A 0 366 336; WO 95/20991 and WO 97/14468 are herewith referred to as examples where suitable applicator devices are described.

An additional feature of the invention is the use of two or more analytical zones which undergo a detectable change after contact with the fluid taken from the outlet opening. Diverse forms of suitable analytical zones are known from the field of disposable test elements. Analytical zones which undergo an optically detectable change are particularly preferred in the scope of the invention for reasons which will be described in more detail. An embodiment of the analytical detection zone that is particularly preferred within the scope of the invention is described in U.S. Pat. No. 6,029,919. With regard to the layers of the test element it is of course also possible to use less complex test elements. Electrochemical test elements can also be used for the invention. Electrochemical test elements such as those described in U.S. Pat. No. 5,288,636 are advantageous compared to measuring cells that operate continuously like those used in the field of ultrafiltration and microdialysis since the drift problem is eliminated.

The use of the term "analytical zone" in contrast to "test element" makes it clear that the analytical zones do not necessarily have to be elements that are separated from one another but that the test zones can indeed be disposed on the same body (test element). In a particularly preferred embodiment of the system according to the invention a tape is used in which the test chemistry is arranged in a band shape and adjacent regions of the tape can be contacted with fluid emerging from the catheter. This also makes it clear that the term analytical zone is not limited to embodiments in which the analytical zones are predefined but that embodiments are particularly advantageous in which the respective analytical zone is not defined until contact with the fluid. As a result positioning problems can be largely circumvented. On the other hand it is, however, also possible to use test elements which are separated from one another, each of which provides one or several analytical zones. As already elucidated it is preferred that disposable embodiments are used for the analytical zones in which an analytical zone that has been used once is not used again. As already eluded to, the analytical zones of the present invention exhibit no drift like that which occurs in the case of flow measuring cells. This is due to the fact that an unused analytical zone is employed and the properties of the analytical zones can be adequately controlled by the manufacturing process as is well-known in the prior art. As a result it is also possible to determine the manufacturing tolerances of the analytical zones at the factory and to store these for example in the form of a bar code in order to increase the accuracy of the analysis by taking into account these variations in the analytical process.

An important aspect of the present invention is a sequential application of liquid onto test zones in order to contact the test zones with liquid from the catheter. This can be achieved especially by bringing together various analytical zones with the outlet opening of the catheter in order to contact the analytical zones with fluid. Bringing together in this sense primarily means moving the analytical zones to the outlet opening so that they can take up fluid there. If, however, the outlet openings are located on a flexible tube it is possible to guide the outlet opening to an analytical zone for the contacting. The term "bringing together" is also intended to encompass processes in which analytical zones for example in the form of a tape, are conveyed past the outlet opening, (while being in contact with the outlet opening or in direct proximity) in order to apply liquid to the analytical zones.

Embodiments are also possible in which liquid is already removed from the catheter by contact alone. This can be achieved in particular with absorbent or capillary-active analytical zones. However, it is advantageous to design the system such that liquid does not emerge from the outlet opening until an underpressure is applied. This enables the application of liquid on the analytical zone to be controlled by regulating the pressure conditions in the system.

Another method of contacting the analytical zones with liquid from the catheter is to move the liquid out of the catheter in portions (dropwise) in such a manner that the fluid portions hit the test zones. This can be achieved in particular by using ink-jet or bubble-jet systems in which the fluid portions are ejected from an outlet opening of the catheter or from a subsequent ejection unit. Reference is made to the well-known printing technologies and to the document U.S. Pat. No. 4,336,544 with regard to a possible design for such an ejection unit.

As already described in connection with U.S. Pat. No. 5,368,029, it is important for monitoring time-dependent changes of the analyte concentration to ensure that liquid of a defined time range reaches an analytical zone and that this liquid is mixed with the least possible amount of liquid from previous time intervals. This can be achieved by the present invention in a comparatively simple manner by using a catheter with an inner cross-section of less than about 0.5 mm. With such small cross-sections there is almost no convection so that liquid moves through the catheter in the form of a bolus. In this connection it is also important to avoid dead volumes in the catheter as far as possible that are caused for example by back tapers at fluid junctions etc. Another measure which is important in this connection relates to the ratio between the volume of liquid that is removed from the catheter and the active inner volume of the catheter. The quantity of liquid that is removed is preferably essentially the same as or larger than the. active catheter inner volume such that the active volume is essentially completely emptied when liquid is removed for application onto an analytical zone. This ensures, on the one hand, that the withdrawn liquid is derived from the time interval between the current withdrawal and the previous withdrawal. The active catheter inner volume refers to the inner space of the catheter which fills with liquid between two liquid withdrawals and which is emptied during a withdrawal. In addition to the geometric design of the catheter inner space, the active catheter inner volume is also determined by liquid barriers such as hydrophobic barriers.

Preferred designs of the catheter and the withdrawal processes are elucidated below on the basis of figures.

Another feature of the invention is an analytical device for analysing the analytical zones after contact with liquid. Such analytical devices are well-known in the prior art for example for blood sugar measuring instruments. Reference is herewith made to the document U.S. Pat. No. 4,852,025 as an example thereof in which transformation of reflection-photometric measurements into concentration values is described. Such an analytical device comprises a light source to illuminate an analytical zone, a detector to detect radiation reflected from the analytical zone and an electronic circuit to convert the detector signals into analyte concentrations. Such an analytical device or an additional application detection device can also advantageously be used to determine whether the analytical zone has been adequately contacted with liquid. However, it is not only possible to detect application of liquid as such onto an analytical zone as described for example in EP 0 256 806 but it is also possible to relatively accurately determine the amount of liquid with which the analytical zone has been wetted. A detection of the wetting of an analytical zone is advantageous within the scope of the present invention for several reasons. On the one hand it enables a check of the operating sequence or even a control of the sequence. In the case of systems which operate with an underpressure to allow liquid to flow out of the outlet opening, the detection of a wetting of or an adequate amount of liquid on the analytical zone can for example be used as a signal to switch off the underpressure and thus also the liquid transport. In addition this also enables this signal to be used to break the contact between the analytical zone and liquid or outlet opening.

Detection of the application of liquid to an analytical zone or detection of the amount of liquid that has been applied to an analytical zone can be achieved in many ways. U.S. Pat. No. 5,114,350 for example describes the monitoring of the surface reflection of a test zone. A similar procedure is also described in U.S. Pat. No. 4,199,261. Furthermore it is known from the document WO 83/00931 that absorbance of radiation by the sample in the infrared range can be used as a measure of the quantity of liquid. The above-mentioned methods can be used within the scope of the present invention.

BRIEF DESCRIPTION OF THE DRAWINGS

FIG. 2: Analytical system with a tape-shaped test element in a perspective view.
FIG. 5: Analytical system with separate units for manual operation.

DETAILED DESCRIPTION OF THE DRAWINGS

Figure 1B:
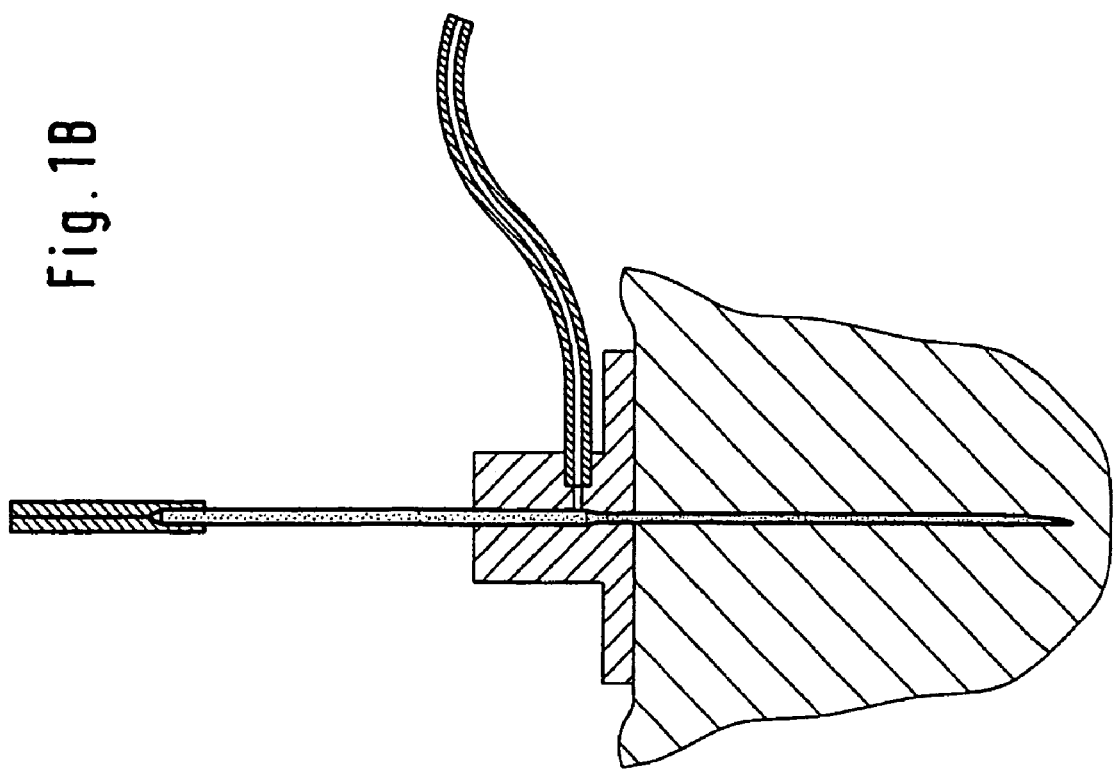
FIG. 1: Construction of a catheter and mode of operation.
Figure 1A:
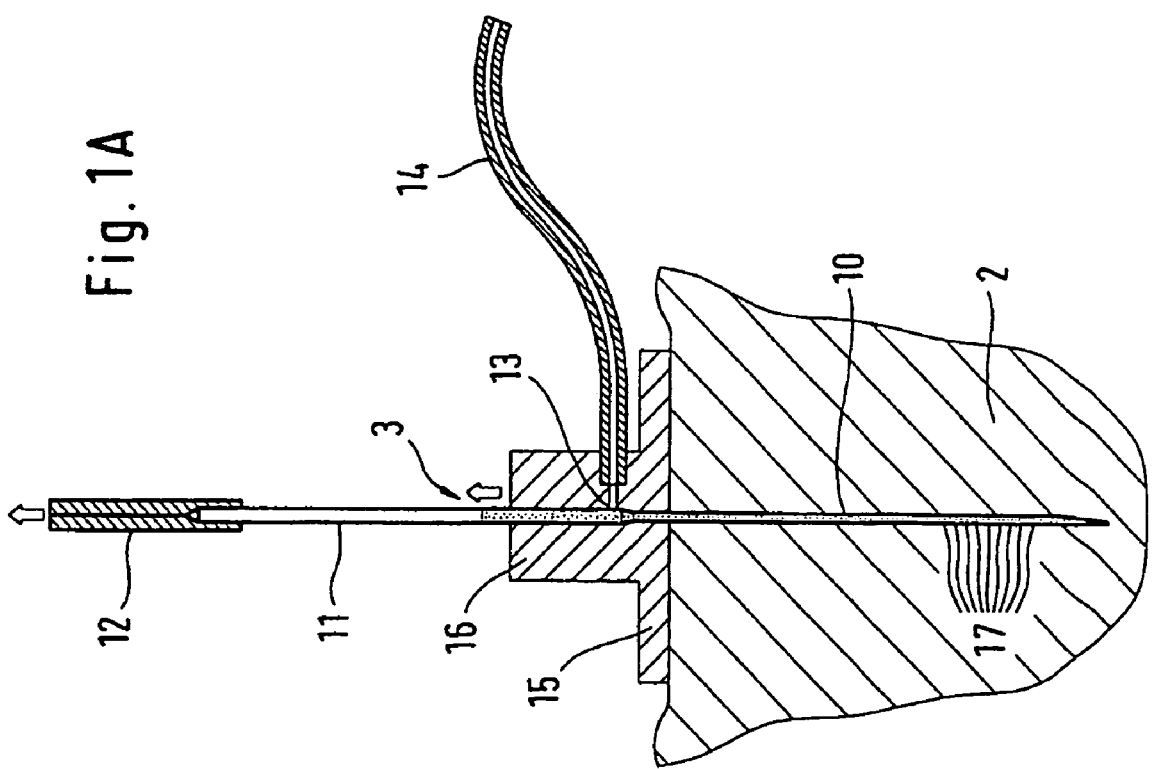

FIG. 1A shows the construction of a preferred catheter according to the present invention. The catheter comprises a hollow needle the distal part (10) of which is implanted in the tissue (2) of a patient. The hollow needle of FIG. 1 is manufactured from stainless steel and has an outer diameter of 500 pm, an inner diameter of 100 pm and a length of 7 mm. Plastics can for example also be used instead of stainless steel. A proximal region (11) with an enlarged inner cross section adjoins the distal part of the hollow needle. As shown in FIG. 1A there is an outlet tube (14) attached to an outlet opening (13) of the hollow needle that is located slightly above the junction region between the implanted region and the proximal region (11). The catheter arrangement is attached by a disk-shaped holder (15) to the body surface. For this purpose the underside of the holder (15) can be provided with an adhesive. In order to further stabilize the arrangement, there is a connecting element (16) above the holder (15) which ensures a fluid-tight coupling of the outlet tube (14) to the outlet opening (13) of the hollow needle (10, 11).

The function of the catheter arrangement is made clear on the basis of the steps shown in figures A-D. Figure IA shows that body fluid, in particular interstitial fluid, enters the implanted region (10) of the hollow needle and is conveyed by capillary forces or by vacuum into the proximal part of the hollow needle (11). In order to allow entry of body fluid, the implanted part (10) has one or several inlet openings (17). These can be located on the needle tip as well as in the wall region of the hollow needle located above this. The length of the implanted part and the position of the inlet openings can be used to determine from which depth body fluid is conveyed. It has proven to be advantageous to convey body fluids from depths of more than 1 mm. It was namely found that the upper skin layers (epidermis and dermis) which together have a thickness of about 1 mm only weakly exchange substances with the interior of the body and especially with the blood stream. It has now become standard practice in diabetes monitoring to determine the metabolic state of the diabetic on the basis of the blood glucose value. This is especially due to the fact that the blood stream supplies the brain and thus hypoglycemia can become an acute threat to life. Consequently it is preferred for the present invention to obtain sample liquid from depths of more than 1 mm, preferably from a depth range of 3 to 10 mm.

As shown in FIG. 1A the body fluid rises in the hollow needle and fills the proximal part (11) of the hollow needle. This usually takes place solely by means of the capillary forces in the hollow needle. For this purpose it is advantageous when the interior region of the hollow needle that is to be wetted by sample liquid is made hydrophilic. In the case of metallic hollow needles this can for example be achieved by applying a hydrophilizing coating. If the capillary forces are not sufficient an underpressure may be applied to convey body fluid from the interior of the body.

In FIG. 1A an air vent (12) is provided at the upper end of the hollow needle which allows air displaced by the body fluid to escape. The air vent is preferably made hydrophobic to prevent body fluid from escaping from the hollow needle. The air vent can for example be a plastic tube made from a hydrophobic polymer such as polyethylene. Another important function of the air vent is to limit evaporation from the hollow needle to avoid blockage of the system by dried up liquid.

FIG. 1B shows the arrangement of FIG. 1A in a filled state ready for the determination. In particular it can be seen that firstly only the interior space of the hollow needle has been filled but not the connecting tube (14). This is achieved by using a connecting tube which has a hydrophobic (or hydrophobically coated) inner wall. Liquid is withdrawn from the filled state of FIG. 1B as shown in figures C and D. Application of an underpressure at the outlet opening (14') of the connecting tube (14) empties the upper widened part of the hollow needle (proximal part 11). Preferably the fluid forces in the system are adjusted such that only the hollow space of the needle above the outlet opening (13) is emptied.

After this space has been emptied, air is sucked in so that the body fluid is moved in the form of a bolus through the connecting tube onto a test zone which is contacted with the outlet opening (14'). The liquid forms a spot (21) on the test zone (20) which has different optical properties than the surroundings and can thus be detected. After the upper inner space of the needle has been emptied, it can be slowly filled again with liquid which subsequently flows from the implanted part. It was found that measurements at intervals of about 5 minutes are completely adequate for monitoring the glucose concentration in humans so that the time period required to fill the upper part of the needle is relatively uncritical.

The system shown in FIG. 1 operates in a batch mode and the volume provided by one discharge can be adjusted by the volume in the upper needle region (11). Alternatively liquid from an implanted needle can be drawn up directly onto a test zone by for example contacting the test zone with an outlet opening.

FIG. 2 shows a system for monitoring concentrations which has a measuring unit (101) and a disposable unit in which test zones are arranged in the form of a test element tape. The connecting tube (114) which can be coupled to the hollow needle as an alternative to the connecting tube (14) in FIG. 1 is shown on the front side of the disposable unit (121). The unit (121) is closed such that an underpressure relative to the outer space can be applied to its inner space via an underpressure connection (118). Two rollers are located in the interior space of the unit (121), of which the first, the dispenser roller (119) carries a reel of tape-shaped analytical agent. The tape is passed from the first roller (119) behind the outlet of the tube (114) and wound onto the second roller, the waste roller (120). The use of an absorbent analytical tape is particularly advantageous within the scope of the invention since liquid is taken up and absorbed which thus avoids contamination of the interior space and also ensures a hygienic disposal of the fluids. In order to operate the roller mechanism the unit (121) has a rubber collar (122) in which a drive rod rotates which is driven by the measuring unit (101) and which winds the analytical tap onto the roller (120) in a step-wise manner. The measuring unit (101) is equipped with an optical head (102) which is inserted into a recess in the disposable unit (121). The optical head (102) has a light source for illuminating the analytical tape and a detector to record the reflected radiation. For this purpose an optical window (103) is provided on the front side of the optical head (102). Since the analytical tape passes through a region that is closed to the external space and to which underpressure can be applied, a transparent window is provided in the unit (121) between the analytical tape and the optical head. The measuring unit also has an electronic analytical unit to determine analyte concentrations based on the reflected radiation. The results that are determined can for example be shown directly on a display or they are passed onto a data processing unit (130) in order to be displayed or transmitted further. The measuring unit also has a connection (105) for the tube (118) and a pump connected to the connector which can be used to pump air out of the disposable unit (121). The measuring unit (101) additionally has a connector (104) for the rubber flange (122) and a drive mechanism for a drive rod that rotates in the flange. After the measuring unit and disposable unit has been connected together and with a catheter, the analyte concentrations are monitored as follows:

Underpressure is applied by the pump of the measuring unit to the disposable unit (121) such that body fluid that has collected in the catheter is sucked via the tube (114) into the unit (121) and passes onto the tape-like test element (analytical tape). After the fluid bolus has been applied to the test zone, the analytical optical system (102) is used to check whether the sample has been correctly applied to the test zone on the basis of the wetted spot. A reflection photometric analysis of the test zone is now carried out using the analytical optics (102) and the measurement result is converted into a concentration value for the analyte concentration. In the case of embodiments which do not operate in a batch mode as described in connection with FIG. 1, the application of fluid on the test zone can also be monitored and when a sufficient amount of fluid is detected, the contact between the test zone and fluid can be interrupted for example by releasing the underpressure. Usually several minutes elapse after the measurement is completed until a short length of the tape-like test element is wound onto the waste roller (120) by actuating the drive mechanism and thus a fresh test zone is moved to the vicinity of the outlet opening of the tube (114). Then liquid can be conveyed by again applying an underpressure and can be taken up by the fresh analytical zone at the outlet position of the tube (114).

Figure 3:
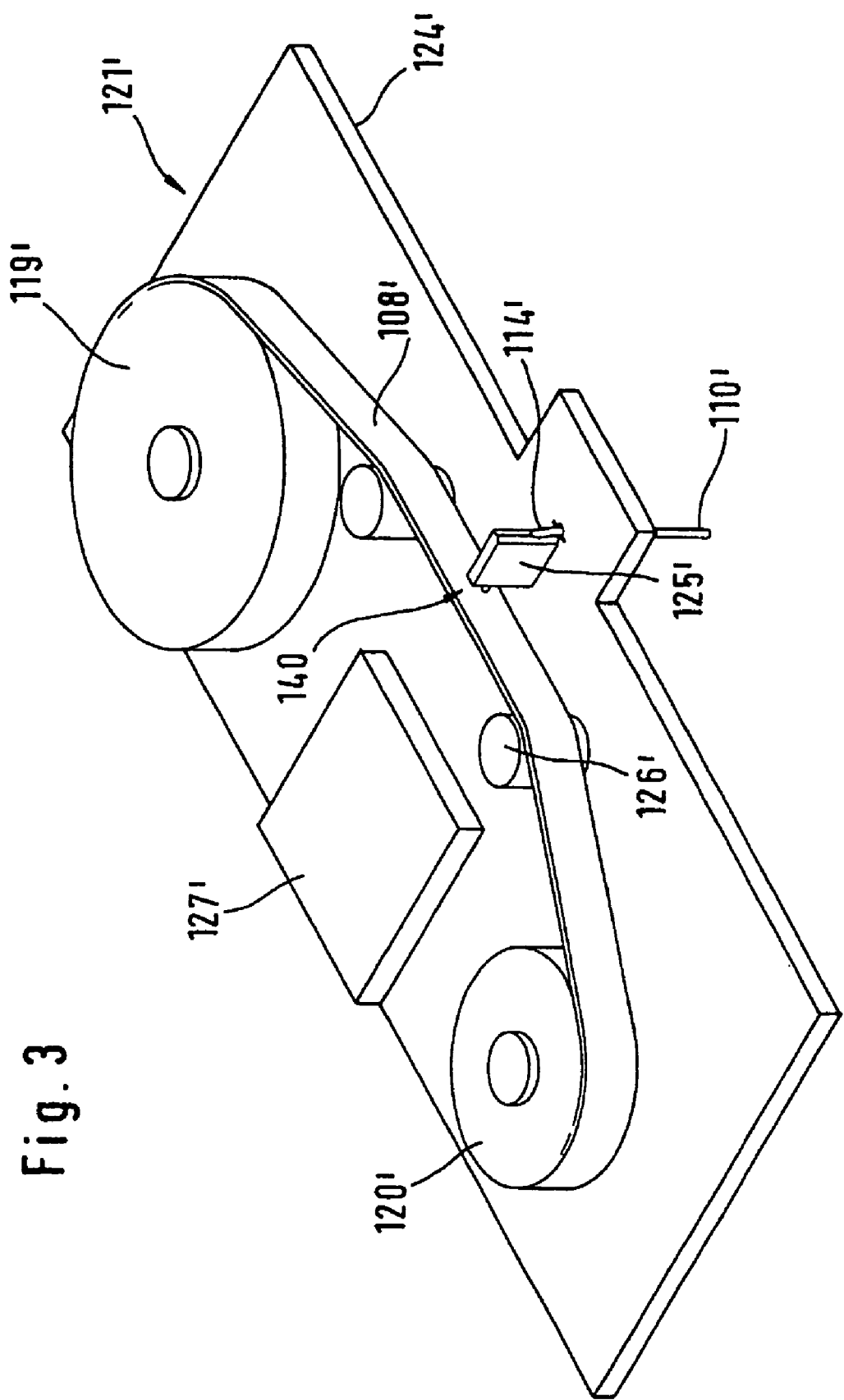
FIG. 3: Cassette with tape-shaped test element and catheter.

FIG. 3 shows a disposable unit (121') that is similar to the disposable unit shown in FIG. 2. The hollow needle (110') that can be implanted in the body is already integrated into this disposable unit. The implantable region (110') is arranged perpendicular to the base surface (124') of the disposable unit. As a result it is possible to implant the hollow needle (110') directly in the body by pressing the base surface of the disposable unit on a body surface to simplify the handling. The hollow needle (110') is joined to the connecting tube (114') which is held by a holder (125'). The tape-like test element (108') is guided past the outlet site of the connecting tube (114') to yield the sample application spot (140) at this position. The analytical tape is guided through rollers (126'). If one measurement is carried out every 5 minutes a 100 cm long analytical tape (108') enables the analyte concentration to be monitored over a period of about 24 hours. In order to prevent ageing of the analytical tape (108') during this period, a desiccant (127') can be provided in the disposable unit (121'). Also due to the ageing of the analytical material it is preferable to seal and store the disposable units (121/121') in a water-tight and vapour-tight manner before use. This can be achieved in a simple manner by sealing the disposable units after manufacture in a plastic laminate.

Figure 4:
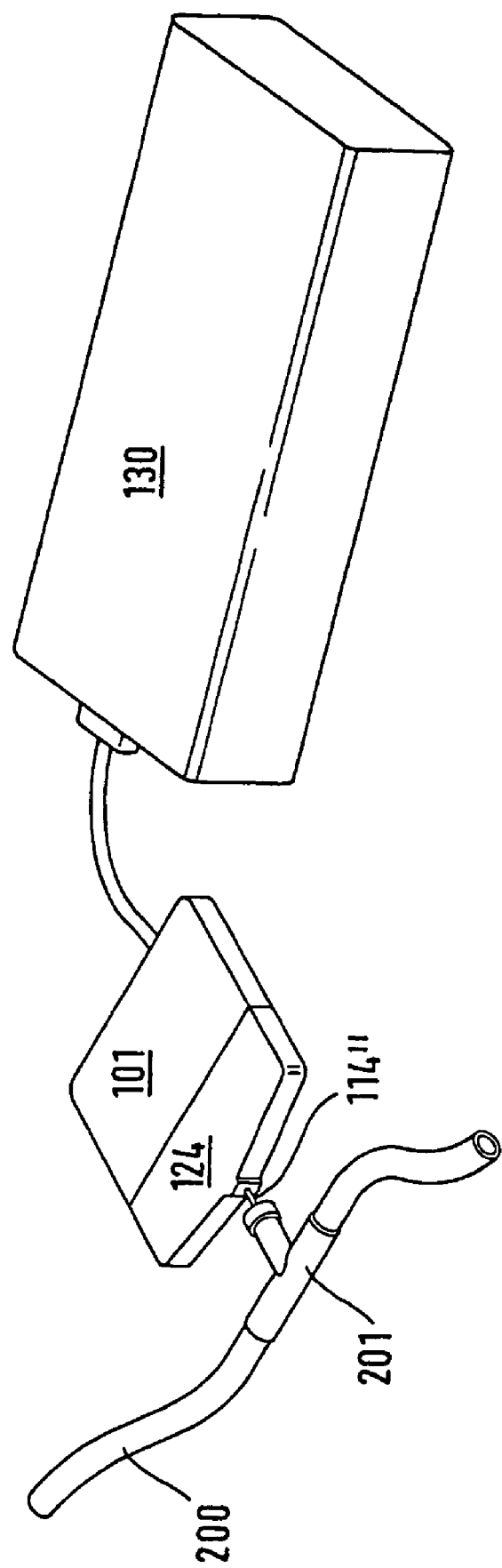
FIG. 4: Analytical system with a coupling to a tube system for blood withdrawal.

FIG. 4 shows a system for monitoring analyte concentrations which can for example be used in the field of emergency medicine. In this field it is usual to place a catheter in a blood vessel in order to withdraw blood to monitor analyte concentrations or to administer medicines. When a blood stream is withdrawn via a fluid line (200), a system can be coupled to it so that the analyte concentration can be monitored directly in the blood. A T-piece (201) can be provided for this via which blood is withdrawn using the withdrawal tube (114"). The monitoring process is similar to that described in the previous figures. However, with the system shown withdrawal is made directly from the blood stream without the batch-wise filling and emptying of a hollow space of a predetermined volume as in FIG. 1.

FIG. 5 shows an embodiment of a monitoring system that is integrated to a lesser degree. The unit (301) carried on the body comprises a catheter (310) that can be implanted in body tissue (2) which is held in a plate (315) that is attached to the body. A holder (302) for test elements with a receiving opening (303) is located above the catheter opening. When a first test element (320) is inserted, the analytical zone (321) is placed above the catheter opening and body fluid emerging from the catheter wets the analytical zone. When a sufficient amount of body fluid has been applied to the test zone which an for example be visually detected by the user, the test element is inserted manually into a conventional analytical instrument (400) and analysed there. As soon as an additional measurement is required, the user can insert a second test element (320') into the opening (303) to wet the test zone (321'). Although the user has to carry out more steps on his own than is the case with a system shown in the previous figures, the embodiment of FIG. 5 has an extremely simple construction and it is possible to use commercially available units for test elements and analytical instruments. A major advantage of the system of FIG. 5 compared to previous commercial systems is that the operator does not have to repeatedly pierce his body for the individual withdrawals of body fluid, but instead the unit (301) provides the necessary body fluid for the analyses as required.

The invention claimed is:

1. System for monitoring the concentration of analytes in body fluids, comprising
   a) a catheter having an implantable region and an outlet opening for the withdrawal of fluid,
   b) a first and a second analytical zone which, after contact with the withdrawn fluid, undergo a detectable change when an analyte is present in the fluid,
   c) a device configured to contact the first analytical zone with fluid from the catheter and to subsequently contact the second analytical zone with fluid from the catheter,
   d) an analytical device configured to analyze the changes on the analytical zones caused by the analyte-containing fluid in order to determine the concentration of an analyte to be monitored, and
   e) a pump configured to apply underpressure to the outlet opening in order to convey liquid,
   wherein the analytical device or an additional application detection device detects the presence of fluid or the presence of an adequate amount of fluid in or on the analytical zones and interrupts the application of the underpressure to the outlet opening based thereon,
   and wherein the first and second analytical zones are areas of a continuous test element, and the continuous test element is a tape.

2. System as claimed in claim 1, wherein the device is configured to contact the first analytical zone and the second analytical zone with the fluid from the catheter by bringing together the outlet opening and the first and second analytical zones.

3. System as claimed in claim 1, wherein the device is configured to contact the first analytical zone and the second analytical zone with the fluid from the catheter by moving portions of the fluid out of the catheter onto the first and second analytical zones via an ejector unit.

4. System as claimed in claim 1, in which the first and second analytical zones are separate objects that are attached to a common support.

5. System as claimed in claim 1, in which the catheter is designed such that no liquid emerges from the outlet opening until the underpressure is applied to the outlet opening.

6. System as claimed in claim 1, further comprising a control device which synchronizes the bringing together of the first and second analytical zones with the outlet opening.

7. System as claimed in claim 1, in which the amount of fluid taken up by either of the first and second analytical zones is essentially equal to or more than the active inner volume of the catheter.

8. System as claimed in claim 1, wherein the device is configured to contact the first analytical zone and the second analytical zone with the fluid from the catheter while the catheter remains implanted.

9. System as claimed in claim 1, wherein the analytical zones are configured to be used once.

10. System as claimed in claim 1, in which the system further comprises a carrying unit for carrying the system on the body and a magazine in which the analytical zones are disposed and which is configured to be inserted into the carrying unit.

11. System as claimed in claim 1, in which the amount of fluid taken up by an analytical zone is less than 100 nl.

12. System as claimed in claim 1, in which the analytical device is configured to optically analyze the first and second analytical zones.

13. The system of claim 1, wherein the fluid is an interstitial body fluid.

14. A system for monitoring the concentration of analytes in body fluids, the system comprising:
 a) a catheter having an implantable region and an outlet opening for the withdrawal of fluid,
 b) a first and a second analytical zone which, after contact with the withdrawn fluid, undergo a detectable change when an analyte is present in the fluid,
 c) a device configured to contact the first analytical zone with fluid from the catheter and to subsequently contact the second analytical zone with fluid from the catheter,
 d) an analytical device configured to analyze the changes on the analytical zones caused by the analyte-containing fluid in order to determine the concentration of an analyte to be monitored, and
 e) a pump configured to apply underpressure to the outlet opening in order to convey liquid,
 wherein the device is configured to contact the first analytical zone and the second analytical zone with the fluid from the catheter in synchronization with the application of the underpressure such that liquid emerging from the outlet opening is taken up by the analytical zones,
 and wherein the first and second analytical zones are areas of a continuous test element, and the continuous test element is a tape.

15. System as claimed in claim 14, in which the analytical device or an additional application detection device is configured to detect the presence of fluid or the presence of an adequate amount of fluid in or on the analytical zones and to interrupt further contact of the analytical zones with fluid.

16. A system for monitoring analyte concentration in body fluid comprising,
 a carrying unit configured to be carried on the body, the carrying unit having a catheter comprising an implantable region and an outlet opening for withdrawing fluid and a tape comprising two or more analytical zones which undergo a detectable change when an analyte is present in the fluid, and a device configured to contact the fluid with the two or more analytical zones while the catheter remains implanted, and
 an analytical device located in the carrying unit or present separately and configured to analyze changes caused by the analyte-containing fluid on the two or more analytical zones in order to determine the concentration of the analyte.

17. The system as claimed in claim 16, wherein the two or more analytical zones comprise at least a first analytical zone and a second analytical zone, and wherein the device is further configured to either bring together the first analytical zone with the outlet opening in order to contact the first analytical zone with fluid and to subsequently bring together the second analytical zone with the outlet opening in order to contact the second analytical zone with fluid, or to apply underpressure to the outlet opening to convey the fluid such that fluid emerging from the outlet opening contacts the first analytical zone and the second analytical zone in synchronization with the application of the underpressure.

* * * * *